United States Patent [19]

Kameswaran et al.

[11] Patent Number: 5,145,986
[45] Date of Patent: Sep. 8, 1992

[54] PROCESS FOR THE MANUFACTURE OF INSECTICIDAL, NEMATICIDAL AND ACARICIDAL 2-ARYL-3-SUBSTITUTED-5-(TRIFLUOROMETHYL)PYRROLE COMPOUNDS FROM N-(SUBSTITUTED BENZYL)-2,2,2-TRIFLUORO-ACETIMIDOYL CHLORIDE COMPOUNDS

[75] Inventors: Venkataraman Kameswaran, Princton Junction, N.J.; David G. Kuhn, Newtown, Pa.

[73] Assignee: American Cyanamid Company, Stamford, Conn.

[21] Appl. No.: 756,639

[22] Filed: Sep. 9, 1991

[51] Int. Cl.$^5$ ............... C07D 207/323; C07D 207/337
[52] U.S. Cl. ................................... 548/531; 548/557
[58] Field of Search .................................. 548/557, 531

[56] References Cited

U.S. PATENT DOCUMENTS

| 5,010,098 | 4/1991 | Brown et al. | 514/424 X |
| 5,030,735 | 7/1991 | Addor et al. | 548/557 X |
| 5,068,390 | 11/1991 | Kuhn et al. | 558/461 |

*Primary Examiner*—Joseph Paul Brust
*Attorney, Agent, or Firm*—John W. Hogan, Jr.

[57] ABSTRACT

There is provided a process for the manufacture of insecticidal, nematicidal and acaricidal 2-aryl-3-substituted-5-(trifluoromethyl)pyrrole compounds via the condensation of an N-(substituted benzyl)-2,2,2-trifluoroacetimidoyl chloride compound with an α-halo-α,β-unsaturated nitrile, ester or nitro compound.

14 Claims, No Drawings

PROCESS FOR THE MANUFACTURE OF INSECTICIDAL, NEMATICIDAL AND ACARICIDAL 2-ARYL-3-SUBSTITUTED-5-(TRIFLUOROMETHYL)PYRROLE COMPOUNDS FROM N-(SUBSTITUTED BENZYL)-2,2,2-TRIFLUORO-ACETIMIDOYL CHLORIDE COMPOUNDS

BACKGROUND OF THE INVENTION

The present invention relates to a process of manufacturing certain 2-aryl-3-substituted 5-(trifluoromethyl)-pyrroles. Although other processes to manufacture such pyrroles are known, previous processes have suffered from certain problems. For example, 2-Aryl-3-substituted-5-(trifluoromethyl)pyrrole compounds useful as insecticides, nematicides and acaricides and the preparation thereof by the reaction of an azalactone with an α-halo-α,β-unsaturated nitrile, ester or nitro compound are described in copending patent application Ser. No. 392,495, filed on Aug. 11, 1989, now abandoned. However, such previously known processes have required for example, lengthy preparations of amino acids o costly starting materials.

It is an object of the present invention to provide a new and efficient process for the manufacture of insecticidal, nematicidal and acaricidal 2-aryl-3-substituted-5-(trifluoromethyl)pyrrole compounds.

SUMMARY OF THE INVENTION

The present invention relates to an efficient process for the manufacture of insecticidal, nematicidal and acaricidal 2-aryl-3-substituted-5-(trifluoromethyl)pyrrole compounds of formula I

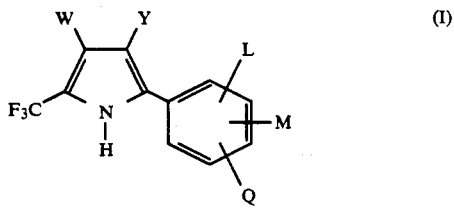

wherein
W is H or $CF_3$;
Y is CN, $NO_2$ or $CO_2R$;
R is $C_1$-$C_4$ alkyl;
L is H, F, Cl or Br;
M and Q are each independently H, F, Cl, Br, I, CN, $NO_2$, $CF_3$, $C_1$-$C_3$ alkyl, $C_1$-$C_3$ alkoxy, $C_1$-$C_3$ alkylsulfonyl, $C_1$-$C_3$ alkylsulfinyl, $C_1$-$C_3$ alkylthio or $R_1CF_2Z$;
Z is $S(O)_n$ or O;
n is an integer of 1 or 2; and
$R_1$ is H, F, $CHF_2$, $CHFCl$ or $CF_3$.

Surprisingly, it has been found that 2-aryl-3-substituted-5-(trifluoromethyl)pyrrole compounds of formula I may be prepared by a single step reaction between an N-(substituted benzyl)-2,2,2-trifluoroacetimidoyl chloride compound of formula II

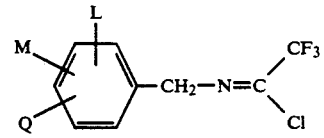

wherein L, M and Q are as described above and an α-halo-α,β-unsaturated nitrile, ester or nitro compound of formula III

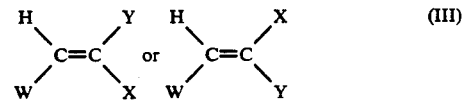

wherein W and Y are as described above; X is Cl, Br or I in the presence of a base and a solvent.

DETAILED DESCRIPTION OF THE INVENTION

The process preferably comprises reacting a formula II N-(substituted benzyl)-2,2,2-trifluoroacetimidoyl chloride compound as described above with at least about one molar equivalent, preferably about one to four molar equivalents of a formula III α-halo-α,β-unsaturated nitrile, ester or nitro compound as described above and at least about one molar equivalent, preferably about one to four molar equivalents, of a base in the presence of a solvent preferably at a temperature range of about 5° C. to 100° C. to form 2-aryl-3-substituted-5-(trifluoromethyl)pyrrole compounds of formula I.

One of the preferred embodiments of the present invention comprises reacting a formula II N-(substituted benzyl)-2,2,2-trifluoroacetimidoyl chloride compound wherein L is H; and M and Q are each independently H, F, Cl, Br, CN, $NO_2$ or $CF_3$ with at least about one molar equivalent, preferably about one to four molar equivalents, of a formula III α-halo-α,β-unsaturated nitrile compound wherein W is H; X is Cl or Br; and Y is CN and at least about one molar equivalent, preferably about one to four molar equivalents, of a base in the presence of a solvent preferably at a temperature range of about 5° C. to 70° C. to form 2-aryl-3-substituted-5-(trifluoromethyl)pyrrole compounds of formula I wherein W is H; Y is CN; L is H; and M and Q are each independently H, F, Cl, Br, CN, $NO_2$ or $CF_3$.

Alternatively, the formula I 2-aryl-3-substituted-5-(trifluoromethyl)pyrrole compounds may be prepared by forming the formula III α-halo-α,β-unsaturated nitrile, ester or nitro compound in situ. This process comprises reacting a formula II N-(substituted benzyl)-2,2,2-trifluoroacetimidoyl chloride compound with at least one molar equivalent of an α,β-dihalo nitrile, ester or nitro compound of formula IV

wherein W is H or $CF_3$; Y is CN, $NO_2$ or $CO_2R$; R is $C_1$-$C_4$ alkyl and X is Cl, Br or I in the presence of at least about two molar equivalents of a base and a solvent.

The process preferably comprises reacting a formula II N-(substituted benzyl)-2,2,2-trifluoroacetimidoyl chloride compound as described above with at least about one molar equivalent, preferably about one to four molar equivalents, of a formula IV α,β-dihalo nitrile, ester or nitro compound as described above and at least about two molar equivalents, preferably two to five molar equivalents, of a base in the presence of a solvent preferably at a temperature range of about 5° C. to 100° C. to form 2-aryl-3-substituted-5-(trifluoromethyl)pyrrole compounds of formula I.

One of the preferred processes of the present invention comprises reacting a formula II N-(substituted benzyl)-2,2,2-trifluoroacetimidoyl chloride compound wherein L is H; and M and Q are each independently H, F, Cl, Br, CN, $NO_2$ or $CF_3$ with at least about one molar equivalent, preferably about one to four molar equivalents, of a formula IV α,β-dihalo nitrile compound wherein W is H, X is Cl or Br; and Y is CN and at least about two molar equivalents, preferably about two to five molar equivalents, of a base in the presence of a solvent preferably at a temperature range of about 5° C. to 70° C. to form 2-aryl-3-substituted-5-(trifluoromethyl)pyrrole compounds of formula I wherein W is H; Y is CN; L is H; and M and Q are each independently H, F, Cl, Br, CN, $NO_2$ or $CF_3$.

The formula I compound may be isolated by conventional techniques such as dilution of the reaction mixture with water and filtration or, alternatively, extraction with a suitable solvent. Suitable extraction solvents include water-immiscible solvents such as ether, ethyl acetate, toluene, methylene chloride, and the like.

Bases suitable for use in the present invention include alkali metal carbonates, $C_1$-$C_4$ trialkylamines, alkali metal hydroxides, alkali metal acetates, 4-dimethylaminopyridine and pyridine. Preferred bases are sodium carbonate, potassium carbonate and triethylamine.

Reaction solvents suitable for use in the present invention include organic solvents for example carboxylic acid amides such as N,N-dimethylformamide, N-methylpyrrolidinone and the like; nitriles such as acetonitrile; halogenated hydrocarbons such as methylene chloride, chloroform, carbon tetrachloride and the like; ethers such as tetrahydrofuran, dioxane and the like; sulfoxides such as dimethyl sulfoxide. Preferred reaction solvents are N,N-dimethylformamide and acetonitrile.

Certain starting formula III α-halo-α,β-unsaturated nitrile, ester and nitro compounds are described in copending patent application Ser. No. 560,403 filed on Jul. 31, 1990, now U.S. Pat. No. 5,068,390, and incorporated herein by reference thereto.

In order to facilitate a further understanding of the invention, the following examples are presented to illustrate more specific details thereof. The invention is not to be limited thereby except as defined in the claims.

EXAMPLE 1

Preparation of 2,2,2-Trifluoro-N-(p-chlorobenzyl)acetimidoyl chloride

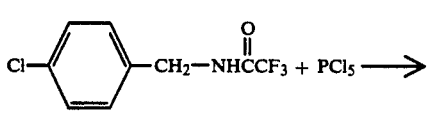

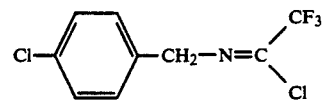

A mixture N-(p-chlorobenzyl)-2,2,2-trifluoroacetamide (100.0 g, 0.421 mol) and phosphorus pentachloride (87.7 g, 0.421 mol) is heated to 100° C., stirred for two hours and vacuum distilled to obtain the title product as a clear colorless liquid (66.3 g, bp 110°–112° C./7.5 mm Hg).

Following the above procedure, but using the appropriately substituted N-benzyl-2,2,2-trifluoroacetamide yields N-(o-chlorobenzyl)-2,2,2-trifluoroacetimidoyl chloride, bp 78°–85° C./2.55 mm Hg and N-(3,4-dichlorobenzyl)-2,2,2-trifluoroacetimidoyl chloride, bp 121°–126° C./2.7 mm Hg.

EXAMPLE 2

Preparation of 2-(p-Chlorophenyl)-5-(trifluoromethyl)pyrrole-3-carbonitrile in the presence of triethylamine and N,N-dimethylformamide

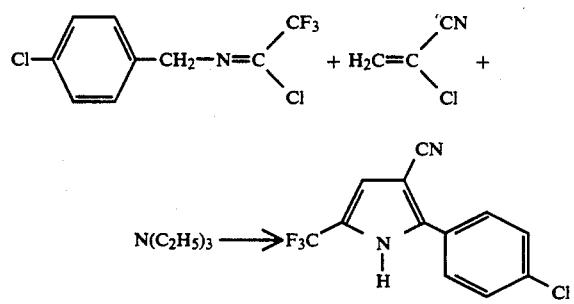

A solution of 2,2,2-trifluoro-N-(p-chlorobenzyl)acetimidoyl chloride (10.0 g, 0.039 mol) and 2-chloroacrylonitrile (4.1 g, 0.047 mol) in N,N-dimethylformamide (50 mL) is cooled to 5° C., treated with triethylamine (8.78 g, 0.086 mol) below 10° C. until half of the triethylamine is added, warmed to room temperature, treated with the remaining triethylamine, stirred at 45° C. for three hours and diluted with water. The aqueous mixture is filtered to obtain a solid which is dried under vacuum to give the title product as a brown solid (8.1 g).

EXAMPLE 3

Preparation of 2-(p-Chlorophenyl)-5-(trifluoromethyl)pyrrole-3-carbonitrile from 2,3-dichloropropionitrile

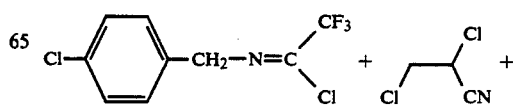

-continued

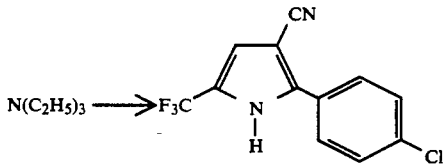

A solution of 2,2,2-trifluoro-N-(p-chlorobenzyl)acetimidoyl chloride (10.0 g, 0.039 mol) and 2,3-dichloropropionitrile (5.81 g, 0.047 mol) in N,N-dimethylformamide is cooled to 5° C. and treated with a solution of triethylamine (17.4 mL, 0.125 mol) in N,N-dimethylformamide. When the addition is half complete, the cooling bath is removed and the reaction mixture is treated with the remaining triethylamine solution, stirred for three hours and poured into water. The aqueous mixture is filtered to obtain a solid which is washed with water and dried under vacuum to give the title product as a pale brown solid (8.0 g).

EXAMPLE 4

Preparation of 2-(p-Chlorophenyl)-5-(trifluoromethyl)pyrrole-3-carbonitrile in the presence of sodium carbonate and N,N-dimethylformamide

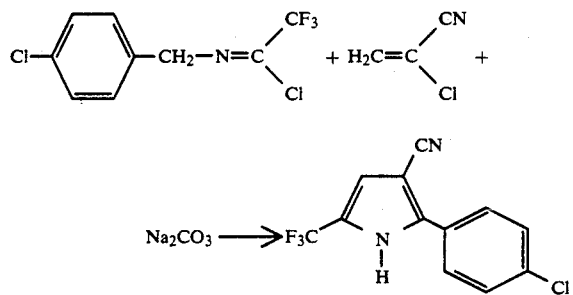

A solution of 2,2,2-trifluoro-N-(p-chlorobenzyl)acetimidoyl chloride (30.0 g, 0.117 mol) and 2-chloroacrylonitrile (12.31 g, 0.141 mol) in N,N-dimethylformamide (150 mL) is treated portionwise with sodium carbonate (27.28 g, 0.257 mol) over one hour (slight exotherm), stirred at 55° C. for two hours and diluted with water. The aqueous mixture is filtered to obtain the title product as a brown solid (25.7 g, mp 228°-229° C.).

EXAMPLE 5

Preparation of 2-(4-Chloro-3-nitrophenyl)-5-(trifluoromethyl)pyrrole-3-carbonitrile

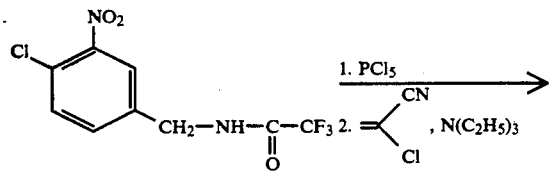

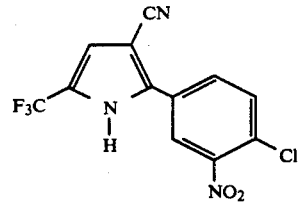

A mixture of N-(4-chloro-3-nitrobenzyl)-2,2,2-trifluoroacetamide (6.0 g, 0.0212 mol) and phosphorus pentachloride (8.9 g, 0.0427 mol) is heated to 100° C. for three hours, concentrated in vacuo to remove excess phosphorus pentachloride and triturated with methylene chloride to obtain a solution of N-(4-chloro-3-nitrobenzyl)-2,2,2-trifluoroacetimidoyl chloride in methylene chloride. The methylene chloride solution is treated with 2-chloroacrylonitrile (2.5 mL, 0.0319 mol) and triethylamine (5.9 mL, 0.0422 mol), stirred overnight at room temperature, diluted with water and extracted with ethyl acetate. The combined organic extracts are washed with water, dried over anhydrous magnesium sulfate and concentrated in vacuo to obtain a residue. Chromatography of the residue using silica gel and a 4:1 hexanes/ethyl acetate solution gives the title product as a yellow solid (0.65 g, mp 258°-260° C.).

Following the above procedure, but using the appropriately substituted N-benzyl-2,2,2-trifluoroacetamide yields 2-(p-nitrophenyl)-5-(trifluoromethyl)pyrrole-3-carbonitrile, mp 258°-261° C. and 2-(2-chloro-5-nitrophenyl)-5-(trifluoromethyl)pyrrole-3-carbonitrile, mp 196°-201° C.

EXAMPLE 6

Preparation of 2-(3,4-Dichlorophenyl)-5-(trifluoromethyl)pyrrole-3-carbonitrile

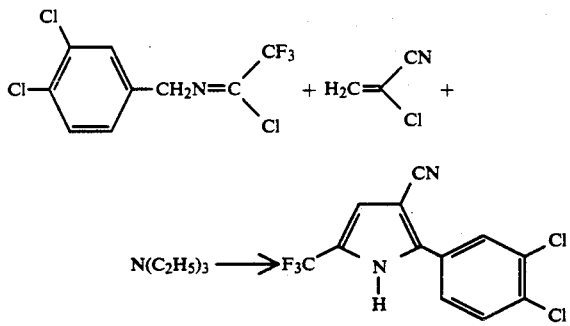

A solution of N-(3,4-dichlorobenzyl)-2,2,2-trifluoroacetimidoyl chloride (20.0 g, 0.069 mol) and 2-chloroacrylonitrile (7.2 g, 0.082 mol) in N,N-dimethylformamide is cooled to 5° C. and treated with a solution of triethylamine (22 mL, 0.16 mol) in N,N-dimethylformamide (38 mL). When the addition is half complete, the cooling bath is removed and the reaction mixture is treated with the remaining triethylamine solution, stirred for two hours and diluted with water. The aqueous mixture is filtered to obtain the title product as a tan solid (18.38 g, mp 230°-232° C.).

EXAMPLE 7

Preparation of 2-(o-Chlorophenyl)-5-(trifluoromethyl)pyrrole-3-carbonitrile

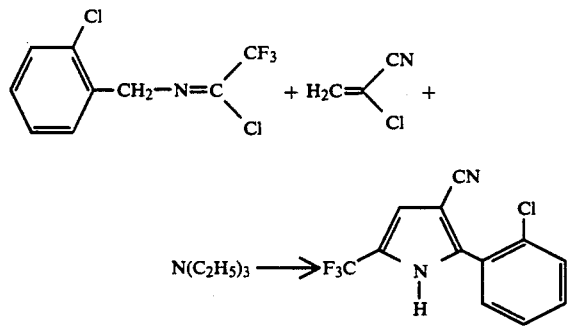

A solution of N-(o-chlorobenzyl)-2,2,2-trifluoroacetimidoyl chloride (10.0 g, 0.039 mol) and 2-chloroacrylonitrile (4.1 g, 0.047 mol) in N,N-dimethylformamide is cooled to 5° C. and treated with a solution of triethylamine (12.0 mL, 0.086 mol) in N,N-dimethylformamide (10 mL). When the addition is one-quarter complete, the cooling bath is removed and the reaction mixture is treated with the remaining triethylamine solution, stirred for three hours, diluted with water and extracted with methylene chloride. The combined organic extracts are washed with water and brine, dried over anhydrous sodium sulfate and concentrated in vacuo to obtain an oil. Flash chromatography of the oil using silica gel and a 1:6 ethyl acetate/heptane solution gives an oil. Crystallization of the oil from heptane gives the title product as a solid (8.5 g, mp 151°–152.5° C.).

We claim:

1. A process for the preparation of a 2-aryl-3-substituted-5-(trifluoromethyl)pyrrole compound having the structural formula

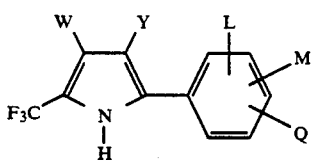

wherein
W is H or $CF_3$;
Y is CN, $NO_2$ or $CO_2R$;
R is $C_1$-$C_4$ alkyl;
L is H, F, Cl or Br;
M and Q are each independently H, F, Cl, Br, I, CN, $NO_2$, $CF_3$, $C_1$-$C_3$ alkyl, $C_1$-$C_3$ alkoxy, $C_1$-$C_3$ alkylsulfonyl, $C_1$-$C_3$ alkylsulfinyl, $C_1$-$C_3$ alkylthio or $R_1CF_2Z$;
Z is $S(O)_n$ or O;
n is an integer of 1 or 2; and
$R_1$ is H, F, $CHF_2$, CHFCl or $CF_3$ which comprises reacting an N-(substituted benzyl)-2,2,2-trifluoroacetimidoyl chloride compound having the structural formula

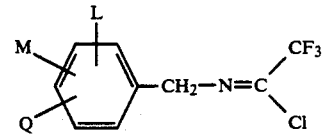

wherein L, M and Q are as described above with at least about one molar equivalent of an α-halo-α,β-unsaturated nitrile, ester or nitro compound having the structural formula

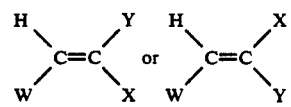

wherein W and Y are as described above, X is Cl, Br or I and at least one molar equivalent of a base in the presence of a solvent to form the 2-aryl-3-substituted-5-(trifluoromethyl)pyrrole compound.

2. The process according to claim 1 wherein the α-halo-α,β-unsaturated nitrile, ester or nitro compound is present in the amount of about one to four molar equivalents and the base is present in the amount of about one to four molar equivalents.

3. The process according to claim 1 wherein the base is an alkali metal carbonate or a $C_1$-$C_4$ trialkylamine and the solvent is N,N-dimethylformamide, acetonitrile, tetrahydrofuran or methylene chloride.

4. The process according to claim 3 wherein the base is triethylamine, sodium carbonate or potassium carbonate.

5. The process according to claim 3 wherein the solvent is N,N-dimethylformamide or acetonitrile.

6. The process according to claim 1 wherein W is H, X is Cl or Br, Y is CN, L is H, and M and Q are each independently H, F, Cl, Br, CN, $NO_2$ or $CF_3$.

7. The process according to claim 1 wherein the temperature of the reaction mixture is about 5° C. to 100° C.

8. A process for the preparation of a 2-aryl-3-substituted-5-(trifluoromethyl)pyrrole compound having the structural formula

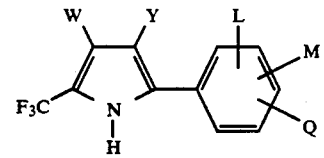

wherein
W is H or $CF_3$;
Y is CN, $NO_2$ or $CO_2R$;
R is $C_1$-$C_4$ alkyl;
L is H, F, Cl or Br;
M and Q are each independently H, F, Cl, Br, I, CN, $NO_2$, $CF_3$, $C_1$-$C_3$ alkyl, $C_1$-$C_3$ alkoxy, $C_1$-$C_3$ alkylsulfonyl, $C_1$-$C_3$ alkylsulfinyl, $C_1$-$C_3$ alkylthio or $R_1CF_2Z$;
Z is $S(O)_n$ or O;
n is an integer of 1 or 2; and
$R_1$ is H, F, $CHF_2$, CHFCl or $CF_3$ which comprises reacting an N-(substituted benzyl)-2,2,2-trifluoroacetimidoyl chloride compound having the structural formula

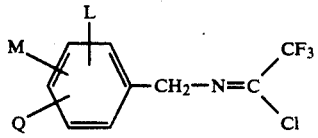

wherein L, M and Q are as described above with at least about one molar equivalent of an α,β-dihalo nitrile, ester or nitro compound having the structural formula

wherein W and Y are as described above, X is Cl, Br or I and at least about two molar equivalents of a base in the presence of a solvent to form the 2-aryl-3-substituted-5-(trifluoromethyl)pyrrole compound.

9. The process according to claim 8 wherein the α,β-dihalo nitrile, ester or nitro compound is present in the amount of about one to four molar equivalents and the base is present in the amount of about two to five molar equivalents.

10. The process according to claim 8 wherein the base is an alkali metal carbonate or a $C_1$-$C_4$ trialkylamine and the solvent is N,N-dimethylformamide, acetonitrile, tetrahydrofuran or methylene chloride.

11. The process according to claim 10 wherein the base is triethylamine, sodium carbonate or potassium carbonate.

12. The process according to claim 10 wherein the solvent is N,N-dimethylformamide or acetonitrile.

13. The process according to claim 8 wherein W is H, X is Cl or Br, Y is CN, L is H, and M and Q are each independently H, F, Cl, Br, CN, $NO_2$ or $CF_3$.

14. The process according to claim 8 wherein the temperature of the reaction mixture is about 5° C. to 100° C.

* * * * *